United States Patent
Nozaki et al.

(10) Patent No.: US 9,517,049 B2
(45) Date of Patent: Dec. 13, 2016

(54) ULTRASONIC PROBE, POSITION DISPLAY APPARATUS AND ULTRASONIC DIAGNOSTIC APPARATUS

(75) Inventors: Mitsuhiro Nozaki, Tokyo (JP); Masafumi Ogasawara, Tokyo (JP)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 13/307,989

(22) Filed: Nov. 30, 2011

(65) Prior Publication Data

US 2012/0136256 A1 May 31, 2012

(30) Foreign Application Priority Data

Nov. 30, 2010 (JP) ................................. 2010-265868

(51) Int. Cl.
*A61B 8/00* (2006.01)
*A61B 8/08* (2006.01)

(52) U.S. Cl.
CPC ............ *A61B 8/4263* (2013.01); *A61B 8/462* (2013.01); *A61B 8/469* (2013.01); *A61B 8/5292* (2013.01); *A61B 8/483* (2013.01); *A61B 8/486* (2013.01); *A61B 8/488* (2013.01)

(58) Field of Classification Search
CPC ....... A61B 8/4263; A61B 8/462; A61B 8/469; A61B 8/483; A61B 8/486; A61B 8/488; A61B 8/5292
USPC .................. 600/437, 438, 443, 459; 382/128
See application file for complete search history.

(56) References Cited

U.S. PATENT DOCUMENTS

| | | | | |
|---|---|---|---|---|
| 5,588,435 A * | 12/1996 | Weng et al. | ................... | 600/443 |
| 6,196,972 B1 * | 3/2001 | Moehring | ...................... | 600/454 |
| 6,251,073 B1 * | 6/2001 | Imran et al. | .................. | 600/443 |
| 7,757,389 B2 | 7/2010 | Nozaki et al. | | |
| 2003/0120155 A1 * | 6/2003 | Sauer et al. | .................. | 600/464 |
| 2005/0090742 A1 | 4/2005 | Mine et al. | | |
| 2005/0113700 A1 | 5/2005 | Yanagihara et al. | | |
| 2005/0228281 A1 * | 10/2005 | Nefos | ........................... | 600/446 |
| 2007/0015412 A1 | 1/2007 | Ito et al. | | |

(Continued)

FOREIGN PATENT DOCUMENTS

CN 2885145 Y 4/2007
JP 11299778 11/1999

(Continued)

OTHER PUBLICATIONS

Japanese Office Action, Application No. 2010-265868, dated Nov. 5, 2012, pp. 3.

(Continued)

*Primary Examiner* — Katherine Fernandez

(57) ABSTRACT

An ultrasonic probe connected to an ultrasonic diagnostic apparatus having a display unit configured to display an ultrasonic image is provided. The ultrasonic probe includes a transducer array aligned in a predetermined direction for and configured to transmit an ultrasonic beam to a target object and receive a reflected ultrasonic beam, a probe display unit fixed to said ultrasonic probe and having a length at least as long as a length of said transducer array, and a display control unit configured to, based on a specific information specified in the ultrasonic image displayed on the image display unit, display a corresponding position of the specific information on said probe display unit.

22 Claims, 10 Drawing Sheets

(56) References Cited

U.S. PATENT DOCUMENTS

| | | | |
|---|---|---|---|
| 2007/0167762 A1* | 7/2007 | Kim et al. | 600/437 |
| 2007/0167808 A1 | 7/2007 | Nozaki | |
| 2008/0205715 A1* | 8/2008 | Halmann | 382/128 |
| 2008/0221446 A1* | 9/2008 | Washburn et al. | 600/437 |
| 2008/0287783 A1* | 11/2008 | Anderson | 600/429 |
| 2009/0024039 A1* | 1/2009 | Wang et al. | 600/459 |
| 2010/0179427 A1* | 7/2010 | Yamamoto | 600/443 |
| 2010/0312120 A1* | 12/2010 | Meier | 600/459 |
| 2012/0157834 A1* | 6/2012 | Lazebnik | 600/437 |

FOREIGN PATENT DOCUMENTS

| | | |
|---|---|---|
| JP | 2001-269337 | 10/2001 |
| JP | 2003169798 | 6/2003 |

OTHER PUBLICATIONS

Unofficial Manual translation of Chinese Office Action issued in connection with corresponding CN Application No. 201110462541.2 on Aug. 18, 2014.

* cited by examiner

ULTRASONIC PROBE, POSITION DISPLAY APPARATUS AND ULTRASONIC DIAGNOSTIC APPARATUS

CROSS REFERENCE TO RELATED APPLICATIONS

This application claims the benefit of Japanese Patent Application No. 2010-265868 filed Nov. 30, 2010, which is hereby incorporated by reference in its entirety.

BACKGROUND OF THE INVENTION

This invention relates to an ultrasonic probe, a position display apparatus and an ultrasonic diagnostic apparatus, in which the ultrasonic diagnostic apparatus displays an ultrasonic image and specifies a specific region, and displays a corresponding position of a transducer of the ultrasonic probe.

An ultrasonic diagnostic apparatus displays the condition of a target object on an image display unit in B-mode image or color Doppler image. If the position relationship between the image display unit and the transducer array of the ultrasonic probe cannot be determined, the operator cannot easily and accurately recognize the position on the target object observed from the ultrasonic probe. A conventional ultrasonic diagnostic apparatus disclosed in Japanese Patent No. 4489237B specifies the position relationship between the image display unit and the transducer array of the ultrasonic probe. The conventional ultrasonic diagnostic apparatus disclosed in Japanese Patent No. 4489237B forms the position marking on a side of a cover of the ultrasonic probe at a regular interval, and displays position guide at a regular interval, which corresponds to the position marking thereof, on the image display unit.

Unfortunately, the position marking and the position guide placed at a regular interval provides rough positions of arbitrary places on the ultrasonic image, and it is difficult to relate the transducer array in the ultrasonic probe and arbitrary places on the ultrasonic image. Also, when the operator indicates position on the surface of the target object using a medical pen for an operation purpose, the ultrasonic image is displayed in an enlarged format. It is preferred that the position relationship between the arbitrary position of the enlarged image and the transducer array of the ultrasonic probe is indicated in an enlarged format.

SUMMARY OF THE INVENTION

The embodiments described herein provide an ultrasonic diagnostic apparatus, in which the apparatus recognizes the position of a specific region in the ultrasonic probe, by the operator setting the specific region on the ultrasonic image displayed on the image display unit. Also, the embodiments described herein relate to an ultrasonic probe and position display apparatus that can display the position of the ultrasonic probe and the corresponding position of the specific region thereof.

In a first aspect, an ultrasonic probe is provided. The ultrasonic probe is connected to an ultrasonic diagnostic apparatus that includes an image display unit for displaying ultrasonic image. The ultrasonic probe includes a transducer array aligned in a predetermined direction, for transmitting an ultrasonic to a target object and receiving reflected ultrasonic, a probe display unit fixed to the ultrasonic probe having length same as or longer than that of the transducer array in the ultrasonic probe, and a display control unit for, based on a specific information specified by the ultrasonic image displayed in the image display unit, displaying a corresponding position of the specific information to the probe display unit.

In a second aspect, an ultrasonic probe is provided. The specific information is both end parts of a site of the target object in the predetermined direction, and the display control unit separates one end part and the other end part for displaying two points on the probe display unit.

In a third aspect, an ultrasonic probe is provided. The specific information is a width of a site of the target object in the predetermined direction, and the display control unit displays a region of the width in the probe display unit.

In a fourth aspect, a position display apparatus fixed to an ultrasonic probe in a removable manner is provided, the ultrasonic probe connected to an ultrasonic diagnostic apparatus including an image display unit for displaying an ultrasonic image. The position display apparatus includes a probe display unit fixed to the ultrasonic probe, including a probe display unit having length same as or longer than that of a transducer array in the ultrasonic probe, and a display control unit, based on a specific information specified by the ultrasonic image displayed in the image display unit, for displaying a corresponding position to the probe display unit. The position display unit is fixed to the ultrasonic probe in a way that the probe display unit corresponds to the transducer array in the direction that the transducer array is aligned.

In a fifth aspect, a position display apparatus is provided. The specific information is both end parts of the site of the target object in the predetermined direction, and the display control unit separates the one end part and the other end part, for displaying two points on the probe display unit.

In a sixth aspect, a position display apparatus is provided. The specific information is a width of the site of the target object in the predetermined direction, and the display control unit displays a region of the width in the probe display unit.

In a seventh aspect, an ultrasonic diagnostic apparatus is provided. The ultrasonic diagnostic apparatus including an image display unit for displaying an ultrasonic image, a specific information input unit for inputting specific information to the ultrasonic image in a predetermined direction displayed in the image display unit an output unit for outputting a signal of the specific information an ultrasonic probe for having a transducer array placed in the predetermined direction, which transmits an ultrasound to a target object and receives reflected ultrasound from the target object, a probe display unit fixed to the ultrasonic probe, including a probe display unit having length same as or longer than that of the transducer array in the ultrasonic probe, and a display control unit, based on a signal outputted from the outputting unit, for displaying a corresponding position to the probe display unit.

In an eighth aspect, an ultrasonic diagnostic apparatus is provided. The specific information includes a first specific information and a second specific information that is different from the first specific information in the predetermined direction, and the display control unit displays the first specific information and the second specific information on the probe display unit in an identifiable manner to the predetermined direction.

In a ninth the aspect, an ultrasonic diagnostic apparatus is provided. The specific information includes the first specific information and the second specific information, that is different from said first specific information in an orthogonal direction to the predetermined direction, and the display control unit displays the first specific information and the second specific information in an identifiable manner to the orthogonal direction.

In a tenth aspect, ultrasonic diagnostic apparatus including a blood flowing region detecting unit for detecting a blood flowing region of the target object is provided. The specific information input unit inputs the blood flowing region detected by the blood flowing region detecting unit as the specific information.

In an eleventh aspect, an ultrasonic diagnostic apparatus is provided. The specific information input unit includes a touch panel fixed to surface of the image display unit.

In a twelfth aspect, an ultrasonic diagnostic apparatus is provided. The specific information is both end parts of a site of the target object in the predetermined direction, and the display control unit separates the one end part and the other end part, for displaying two points on the probe display unit.

In a thirteenth aspect, an ultrasonic diagnostic apparatus is provided. The specific information is a width of a site of the target object in the predetermined direction, and the display control unit displays a region of the width in the probe display unit.

DETAILED DESCRIPTION OF THE INVENTION

Hereinafter, exemplary embodiments will be described in detail with reference to the accompanying drawings. The scope of the present invention is not limited to embodiments described herein.

Configuration of the Ultrasonic Diagnostic Apparatus

Figure 1:
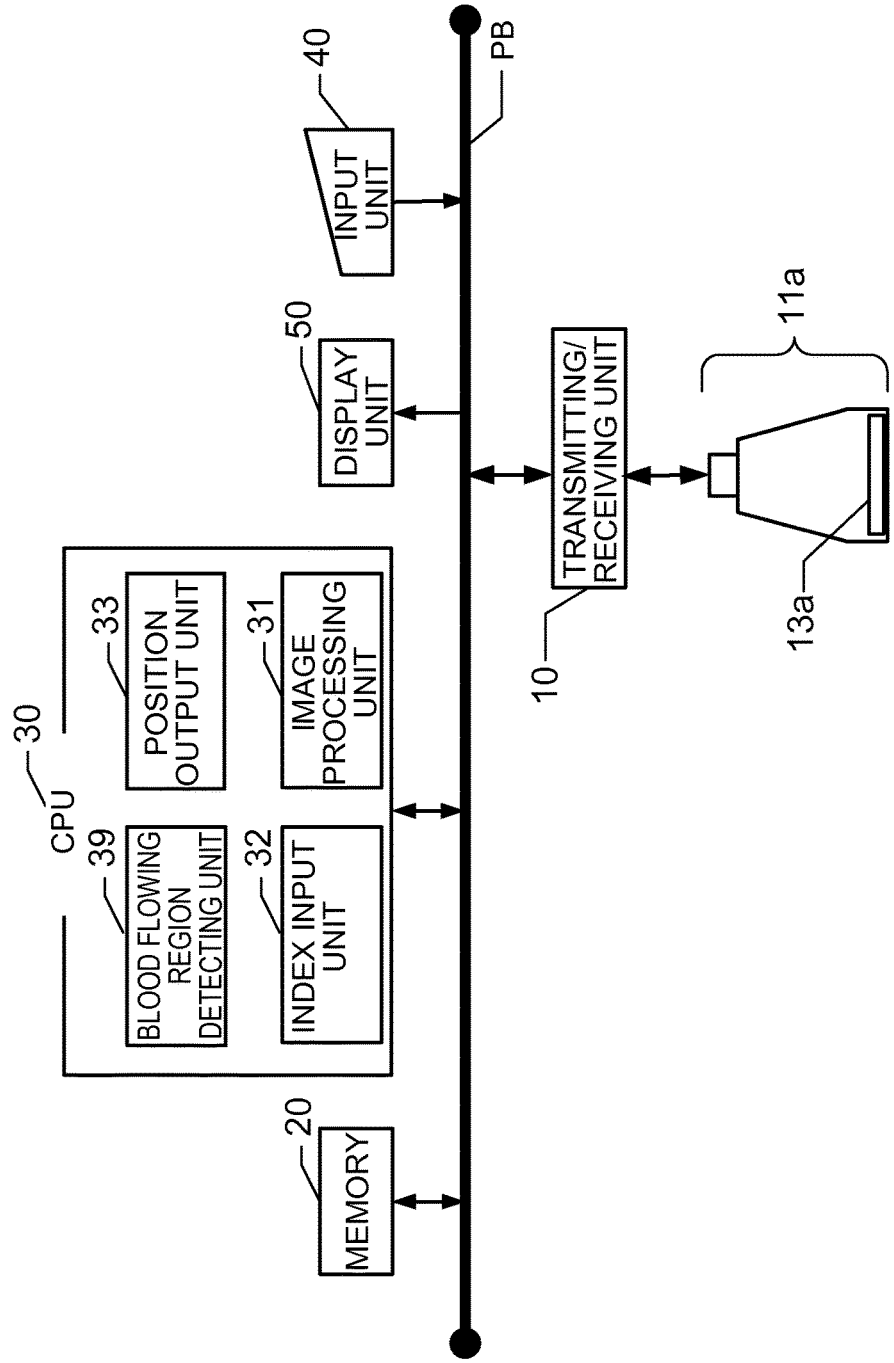
FIG. 1 is a block diagram illustrating the overall configuration of an exemplary ultrasonic diagnostic apparatus.

FIG. 1 is a block diagram illustrating the overall configuration of an ultrasonic diagnostic apparatus.

Ultrasonic diagnostic apparatus 100 includes a parallel bus PB, a transmitting/receiving unit 10 connected to parallel bus PB, a linear-shaped ultrasonic probe 11a, a memory 20, a CPU (Central Processing Unit) 30, an input unit 40 and a display unit 50.

Parallel bus PB is a communication means for transmitting/receiving all sorts of data, and can be replaced with other communication means, such as a serial bus. CPU 30 includes an image processing unit 31, an index input unit 32, a position output unit 33 and a blood flowing detecting unit 39. CPU 30 controls the ultrasonic diagnostic apparatus 100 and processes all sorts of data.

A removable linear ultrasonic probe 11a is connected to the transmitting/receiving unit 10. The transmitting/receiving unit 10 drives the linear ultrasonic probe 11a at a predetermined scan condition for scanning the ultrasonic beam of each sound ray. Also, the transmitting/receiving unit 10 performs the analog/digital conversion to the echo signal, received from the linear ultrasonic probe 11a, into the sound ray data. The sound ray data is outputted to the image processing unit 31. The sound ray data outputted from the transmitting/receiving unit 10 can be stored into the memory unit 20.

The linear ultrasonic probe 11a includes a transducer unit 12a and a probe display unit 13a. The transducer unit 12a and the probe display unit 13a are embedded into the linear ultrasonic probe 11a, and the transducer unit 12a and the probe display unit 13a communicate with the transmitting/receiving unit 10 and the CPU 30 through the parallel bus PB. A linear ultrasonic probe 11a will hereinafter be described in detail.

The image processing unit 31 creates B-mode image or Doppler image of the sound ray data by image processing. The image processing unit 31 processes logarithmic compression and envelope demodulation processing to the sound ray data, and creates B-mode ultrasonic image EG in real-time (refer to FIG. 3 to FIG. 7). Also, the Doppler image extracts the phase variation information from the reflecting ultrasonic echo signal, calculates blood flowing information such as average velocity of average frequency value of the frequency shift, power value and dispersion, in real-time, and arranges color for displaying on top of the B-mode image. The image processing unit 31 can create the B-mode image and the Doppler image based on the sound ray data stored in the memory 20.

The index input unit 32 can input an index on a desired position, in correspondence to the ultrasonic image EG (refer to FIG. 3 to FIG. 7) displayed in the display unit 50. The index input unit 32 receives signal of the movement of a track ball from the input unit 40, for moving the index to the desired position on the ultrasonic image EG. When the operator inputs one point for the desired position, one specific index MK1 (refer to FIG. 3 to FIG. 5) is displayed, and when the operator inputs two points for the desired position, either one specific region MA (refer to FIG. 6 and FIG. 7) or two specific indices MK1 and MK2 (refer to FIG. 6 and FIG. 7) can be selected. Also, when the operator indicates three or more positions, a plurality of specific indices MK or a plurality of regions MA can be selected. An index input unit 32 will hereinafter be described in detail.

The position output unit 33 transmits the signal of the specific index MK set in the index input unit 32, to the probe display unit 13a. The position output unit 33 decodes specific index MK, set in the index input unit 32, to the coordinate system of the probe display unit 13a. The decoded signal of the specific index MK is transmitted to the probe display unit 13a through the parallel bus PB. Probe display unit 13a displays the decoded signal of the specific index MK at desired position and form. The position output unit 33 can display the specific region MA on the probe display unit 13a in a same manner.

The blood flowing region detecting unit 39 acquires Doppler information calculated in the image processing unit 31, and detects blood vessel in the blood flowing region. The blood flowing region detecting unit 39 will hereinafter be described in detail in the fourth embodiment.

The input unit 40 is an inputting means using track ball, mouse or keyboard, and it includes touch panel fixed on the display unit 50, which will hereinafter be described.

The memory 20 contains memory storage unit for storing the sound ray data, ultrasonic image EG, all sorts of data and program. In all sorts of data, index positions which will hereinafter be described are included. All sorts of data, such as ultrasonic images EG and index positions, and all sorts of programs are stored and accessed on a necessary basis. The memory 20 can be connected to outside by network.

Display unit 50 is an image display unit for displaying ultrasonic image EG created by the image processing unit 31 using an image display apparatus, such as crystal display. Also, the image display apparatus for the display unit 50 may contain the inputting means such as touch panel. The touch panel functions as an inputting unit 40.

First Embodiment

Hereinafter, a first embodiment is explained referring to FIG. 2 to FIG. 7. In the first embodiment, an explanation is made based on using the linear ultrasonic probe 11a.

Configuration of a Linear Ultrasonic Probe

Figure 2:
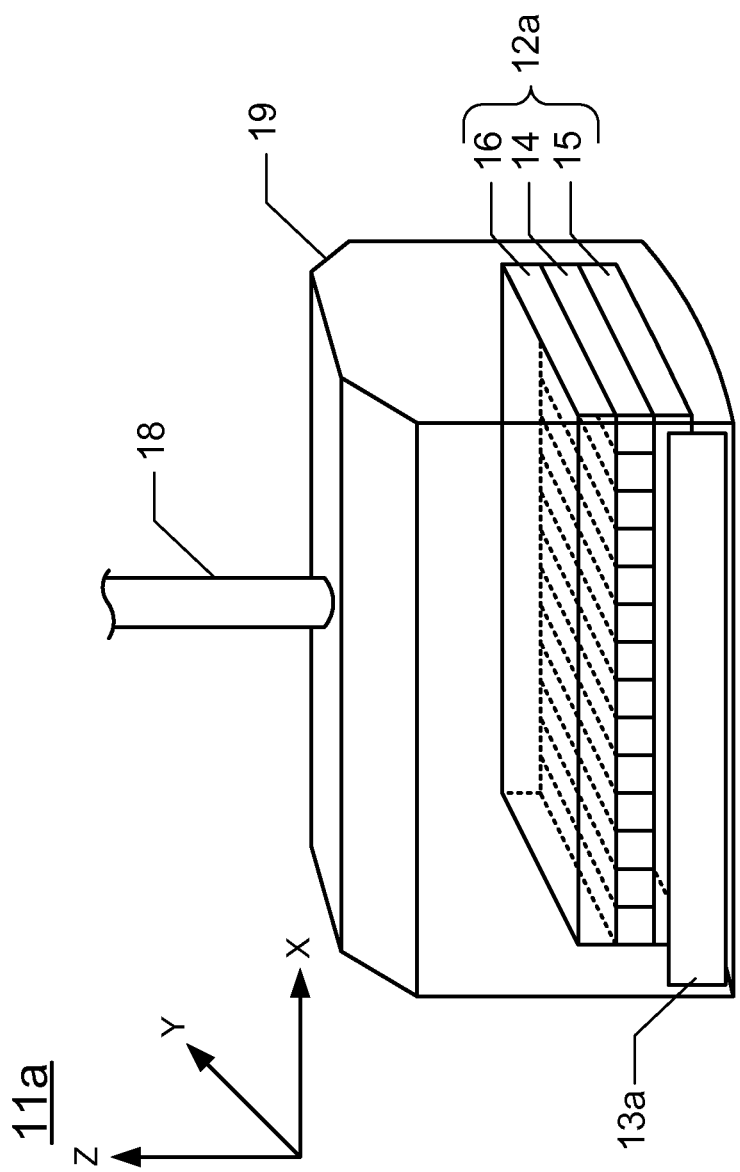
FIG. 2 is a perspective view of the linear ultrasonic probe shown in FIG. 1.

A linear ultrasonic probe 11a is explained in detail. FIG. 2 is a perspective view of the linear ultrasonic probe 11a.

As shown in FIG. 2, a linear ultrasonic probe 11a includes a transducer unit 12a, probe display unit 13a, cable 18 and case 19 for storing the transducer unit 12a and the probe display unit 13a. FIG. 2 shows the inner configuration of the linear ultrasonic probe 11a to provide a better understanding.

Transducer unit 12a transmits and receives the ultrasonic beam scanned onto the target object, for acquiring the ultrasonic image EG. The surface of the transducer unit 12a of the linear ultrasonic probe 11a contacts to the surface of the body of a target object, and the ultrasonic beam is transmitted and received through the transducer unit 12a.

The transducer unit 12a includes the linear transducer 14 consisting of a plurality of transducer element, a matching layer 15 for matching impedance between the linear transducer unit 12a and the target object, and the backing material 16 which absorbs the backward vibration of the target object and minimizes the pulse wave of an ultrasonic beam.

The linear transducer 14 forms a plurality of rectangle-shaped transducers in a predetermined direction, facing toward the surface of the target object, and ultrasonic beam is transmitted when electrical voltage is applied. Also, when the ultrasonic beam is transmitted toward the body tissue of a target object, the transducer unit 12a can receive the echo signal thereof. The linear transducer 14 performs electric scan along the alignment. The linear transducer 14 consists of, for example, PZT (lead zirconate titamate) ceramics, which convert electric signal into the ultrasonic beam for transmitting and converts received echo signal into electric signal.

The matching layer 15 is formed with materials having impedance intermediate between the linear transducer 14 and the target object, for minimizing acoustic impedance between the linear transducer 14 and the body tissue, and suppresses reflection of the ultrasonic beam to the linear transducer 14.

Backing material 16 absorbs acoustic energy radiated from the linear transducer 14, and is formed by, for example, epoxy resin, which has large attenuation coefficient and low impedance.

Probe display unit 13a consists of a flat-panel display element, such as organic EL display or crystal panel display. The display element of the flat panel has a long shape in the predetermined direction of the linear transducer 14. Probe display unit 13a consists of a display region that is about the same length of or longer than the length of the transducer of the linear transducer 14. Probe display unit 13a can display similar index as the index displayed in the display unit 50 of the ultrasonic diagnostic apparatus 100. Probe display unit 13a is not limited to the display element of the flat panel. For example, 20-40 LED (Lazar Emitting Diode) at 3 mm diameter can be arranged in the predetermined direction on one row. When LED is used as the probe display unit 13a, the LED is arranged at either the same length or longer than the transducer of the linear transducer 14. Also, when using LED, similar form of the index as displayed on the display unit 50 cannot be displayed. Instead, index is displayed by displaying its corresponding position or using different colors.

Inputting Position of Index on an Ultrasonic Image

Hereinafter, an operation of inputting the index position on the ultrasonic image displayed in the display unit 50 is explained, referring to FIG. 3 to FIG. 7. FIG. 3 to FIG. 7 describes the ultrasonic image EG and the probe display unit 13a for a better understanding.

Displaying Coordinates in Indices

A method of an operator indicating one point on the ultrasonic image EG using the input unit 40, and displaying the specific index MK1 on the index input unit 32 based on one point, for setting the display index PP1 on one position of the probe display unit 13a, will be explained below.

Figure 3A:
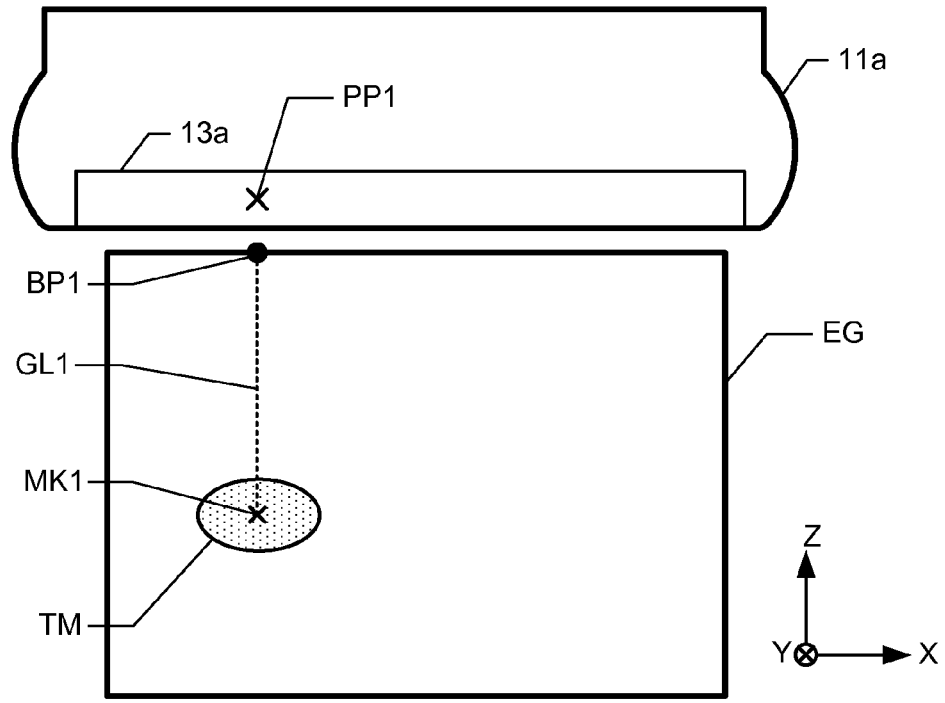
FIG. 3(a) is a diagram illustrating the setting of the puncturing route GL1, puncturing from the tumor TM to the surface of a target object vertically.
Figure 3B:
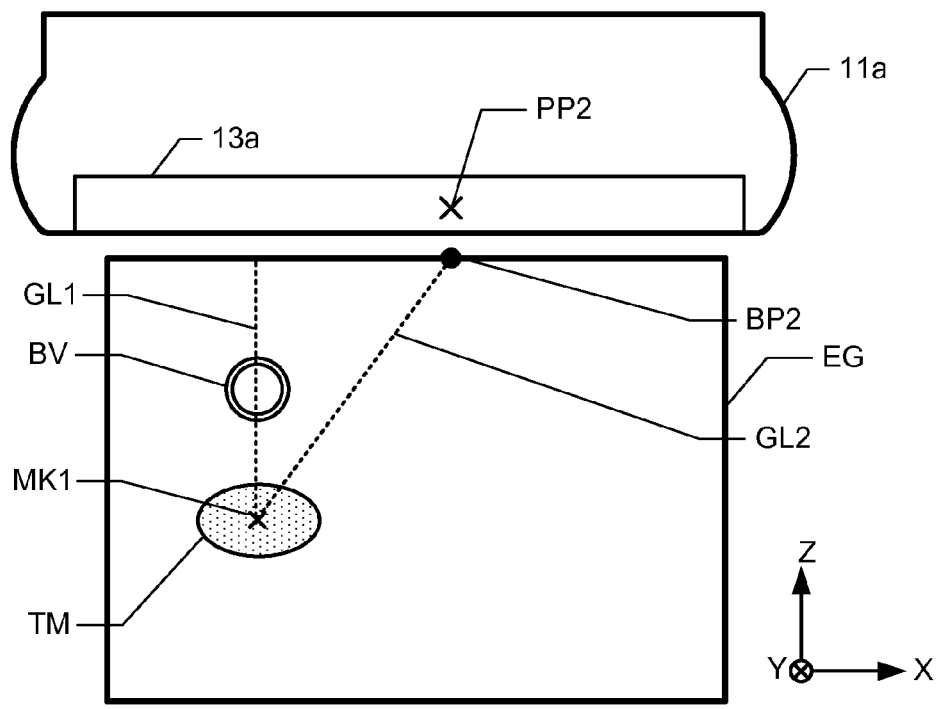
FIG. 3(b) is a diagram illustrating the setting of the puncturing route GL2, puncturing from the tumor TM to the surface of a target object at a predetermined angle.

When inputting one point on the index input unit 32, the point is used for puncturing towards a tumor TM, or a luminal structure such as a blood vessel or nerve block. Puncturing a tumor TM is explained in detail with reference to FIG. 3. FIG. 3 is a perspective view describing the relationship between one specific index MK1 and the display index PP1.

For example, for diagnosing body tissue, the operator punctures towards a tumor TM using the ultrasonic diagnostic apparatus 100. In diagnosing body tissue, a needle punctures towards the tumor of the target object, for extracting the tumor from using the needle. When diagnosing body tissue, the operator observes the ultrasonic image EG indicating the tumor TM through the display unit 50 of the ultrasonic diagnostic apparatus 100, and punctures the needle towards the tumor of the target object. In this case, the index input unit 32 sets the position of tumor TM and the puncturing route GL on the ultrasonic image EG.

The puncturing route GL can be set both vertically or at a certain angle to the surface of the body. FIG. 3(a) is a diagram illustrating the setting of route GL1, puncturing from the tumor TM to the surface of a target object vertically. In FIG. 3(a), the coordinate in the X-axis direction of the probe display unit 13a and the coordinate in the X-axis direction of the ultrasonic image EG are displayed at the same magnification.

As shown in FIG. 3(a), the operator indicates the center of the tumor TM on the ultrasonic image EG displayed in the display unit 50, using the touch panel or the input unit 40 such as mouse. The index input unit 32 sets the specific index MK1 on the center of the tumor TM. In FIG. 3(*a*), the specific index MK1 is selected with "x" mark, which represents the shape of the index. This specific index MK1 includes the shape information of an index, and the coordinate information to the X-axis and Z-axis direction. Then, the index input unit 32 calculates the vertical puncturing route GL1, connecting the specific index MK1 and the surface of the body vertically, for puncturing the needle, and displays the route GL1 on the ultrasonic image EG. Also, the index input unit 32 assigns the intersection point of the puncturing route GL1 and the surface of the body as the border position BP1. The border position BP1 is a position displayed in the probe display unit 13*a*. The position output unit 33 decodes the coordinates of the border position BP1, and converts to the coordinates corresponding to the probe display unit 13*a*. In FIG. 3(*a*), the decoded coordinate position to the X-axis direction may be displayed only, since the probe display unit 13*a* can only display one-dimensional direction. In the probe display unit 13*a*, the display index PP1, having the same shape as the specific index MK1, is displayed in a position corresponding to the border point BP1.

The display index PP1 contains the coordinate information and the information of a shape of the index. The operator can confirm the index "x", an index with a same shape as the index set in the specific index MK1, on the probe display unit 13*a*. Thereby, the operator can mark on the surface of the body of the target object using the medical pen, for puncturing the needle on accurate position.

FIG. 3(*b*) is a diagram illustrating the setting of route GL2, puncturing from the tumor TM to the surface of a target object at predetermined angle. In FIG. 3(*b*), the coordinate in the X-axis direction of the probe display unit 13*a* and the coordinate in the X-axis direction of the ultrasonic image EG are displayed at the same magnification.

As displayed in FIG. 3(*b*), the operator indicates the center of the tumor TM on the ultrasonic image EG displayed in the display unit 50, using the input unit 40 such as the touch panel or mouse. The index input unit 32 sets the specific index MK1 on the center of the tumor TM. In FIG. 3(*b*), the specific index MK1 is also selected with "x" mark, which represents the shape of the index. Then, the index input unit 32 calculates the vertical puncturing route GL1, connecting the specific index MK1 and the surface of the body vertically, for puncturing a needle, and displays the route GL1 on the ultrasonic image EG.

The operator observes the puncturing route GL1, and if there is a region that the operator wants to avoid puncturing along the puncturing route GL1, such as blood vessel BV, the operator is able to set the puncturing route GL2 at an arbitrary angle, to avoid puncturing such region. The index input unit 32 calculates the puncturing route GL2, which punctures from the surface of the body of the target object to the specific index MK1 at an arbitrary angle, and displays the puncturing route GL2 on the ultrasonic image EG. When puncturing the needle into the target object, a puncturing guide attachment might be fixed onto the linear ultrasonic probe 11*a*. Since the puncturing guide attachment provides a predetermined angle for puncturing the needle, the index input unit 32 can calculate the puncturing route GL2 with the angle of the puncturing guide attachment, instead of an arbitrary angle.

Also, the index input unit 32 can calculate the border position between the puncturing route GL2 and the surface of the body, as a border position BP2. The border position BP2 is a position displayed by the probe display unit 13*a*, and the position output unit 33 decodes the coordinate of the border position BP2 and converts to coordinates corresponding to the probe display unit 13*a*. In the probe display unit 13*a*, the display index PP2, having the same shape as the specific index MK1, is displayed in a position corresponding to the border point BP2. The border position BP is important if the puncturing angle is not vertical to the surface of the body. If the puncturing angle is vertical to the surface of the body, the coordinate of the specific index MK1 can be decoded, instead of decoding the border position BP2. Moreover, it is not always necessary to display the border position BP on the ultrasonic image EG.

The operator can confirm the index "x", an index with a same shape as the index set in the specific index MK1, on the probe display unit 13*a*. Therefore, the operator can mark on the surface of the body of the target object using the medical pen, for puncturing the needle on accurate position.

Figure 4:
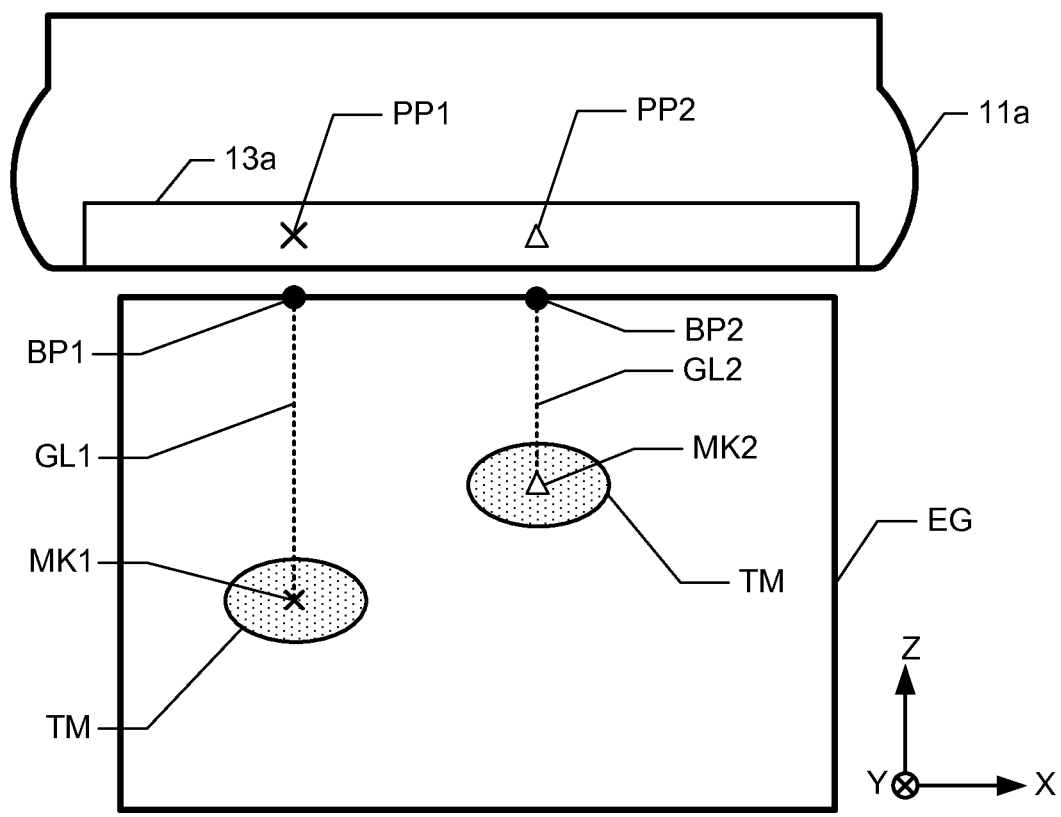
FIG. 4 is a diagram illustrating the setting of specific indices MK1 and MK2 onto two tumors, and indicating the displayed indices PP1 and PP2 to corresponding places.

FIG. 4 is a diagram illustrating the setting of specific indices MK1 and MK2 onto two tumors displayed in the ultrasonic image on the display unit 50, and indicating the displayed index PP1 and PP2 to two corresponding places of the probe display unit 13*a*.

If it is necessary to puncture a plurality of tumors, the operator sets a plurality of specific indices MK. The operator indicates the center of each tumor using the input unit 40. The index input unit 32 sets specific indices MK1 and MK2 based on the input thereof. Display indices PP1 and PP2 include the coordinate information and the information of the shape of each index. In FIG. 4, the specific index MK1 is selected with "x" mark, and the specific index MK2 is selected with "Δ" mark. When the index input unit 32 indicates different shape to each of a plurality of specific index MK, the operator will not mistake each index, even if three or more specific indices MKs are set on the same ultrasonic image EG.

Then, the index input unit 32 calculates the vertical puncturing routes GL1 and GL2, connecting the specific index MK1 and MK2 respectively, and the surface of the body vertically, for puncturing the needle, and displays the route GL1 and GL2 on the ultrasonic image EG. Also, the index input unit 32 assigns the intersection points between the puncturing routes GL1 and GL2 respectively, and the surface of the body as the border position BP1 and BP2. The border positions BP1 and BP2 are positions displayed in the probe display unit 13*a*. The position output unit 33 decodes the coordinates of the specific indices MK1 and MK2 and converts to the coordinates corresponding to the probe display unit 13*a*. In the probe display unit 13*a*, the display index PP1 is displayed with "x" mark, a same shape as the specific index MK1, at the position corresponding to the border position BP1. Also, the display index PP2 is displayed with "Δ" mark, a same shape as the specific index MK2, at the position corresponding to the border position BP2.

The operator can confirm indices ("x" and "Δ"), indices with a same shape as the index set in the specific indices MK1 and MK2, on the probe display unit 13*a*. Thereby, the operator can mark on the surface of the body of the target object using the medical pen, for puncturing the needle on accurate position. By the way, the specific index MK1 and its corresponding display index PP1 were indicated with "x" mark, and the specific index MK2 and its corresponding display index PP2 were indicated with "Δ" mark. However the shapes are not limited to above selections; the specific index MK and the display index PP can be designated with the same shape, or can be set in a separate color for distinction.

Although it is not described specifically, the puncturing routes GL1 and GL2 which are vertical to the surface of the body as indicated in FIG. 4 can be set with an arbitrary angle, as displayed in FIG. 3(*b*). FIG. 3(*a*), FIG. 3(*b*) and FIG. 4 display the coordinates of the probe display unit 13*a* in the X-axis direction and the ultrasonic image EG in the X-axis direction at the same magnification. The example of displaying the ultrasonic image EG in an enlarged image will be described hereafter.

Figure 5A:
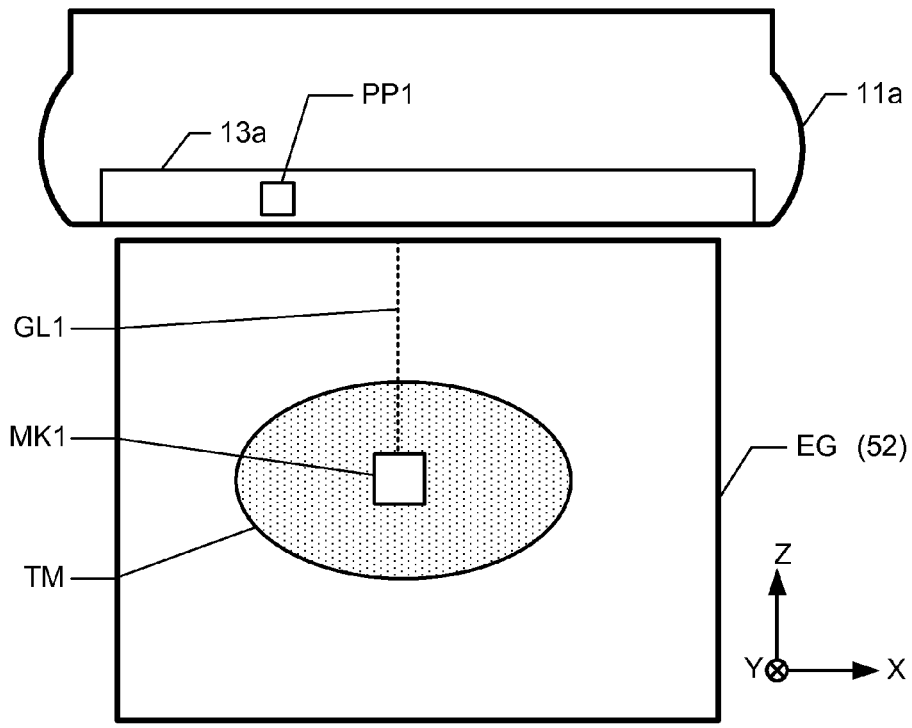
FIG. 5(a) is an example of indicating the specific index MK1 by using the enlarged ultrasonic image EG.
Figure 5B:
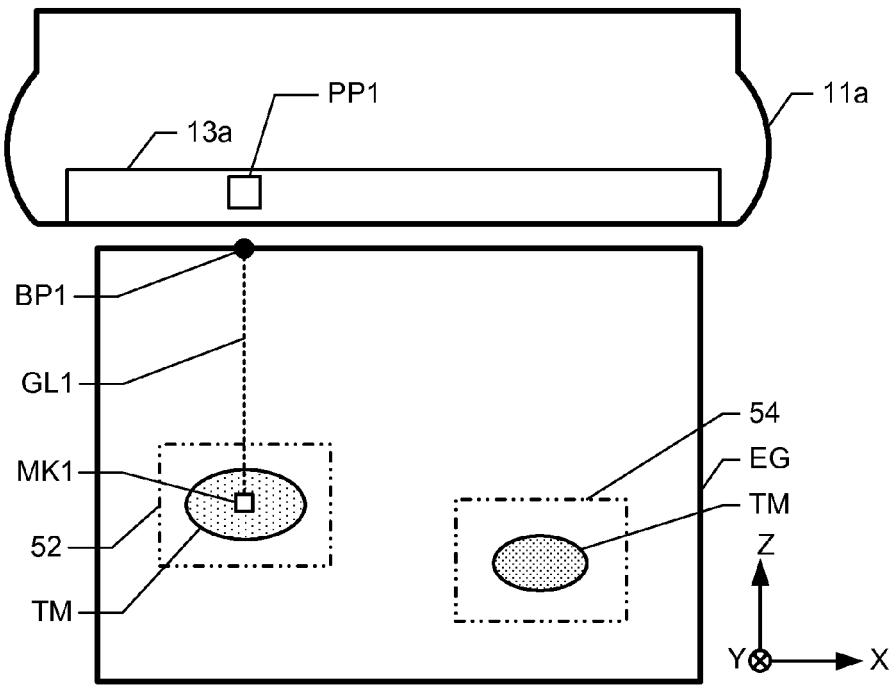
FIG. 5(b) is a diagram of the ultrasonic image EG of FIG. 5(a) displayed at the same magnification.

FIG. 5(*a*) is an enlargement of a part of the ultrasonic image EG. FIG. 5(*a*) displays the enlarged ultrasonic image EG and the probe display unit 13*a* on alignment.

When the operator observes the tumor TM in detail, the operator may display a part of the ultrasonic image EG (i.e. sample area 52) in an enlargement. Then, the operator indicates a center of the tumor TM on the enlarged ultrasonic image EG. The index input unit 32 sets the specific index MK1 on the center of the tumor TM. In such cases, the specific index MK1 is indicated with "□" mark, as indicated in FIG. 5(*a*). Then, the index input unit 32 calculates the vertical puncturing route GL1, connecting the specific index MK1 and the surface of the body vertically, for puncturing a needle, and displays the route GL1 on the ultrasonic image EG. The index input unit 32 calculates the intersection of the puncturing route GL1 and the surface of the body as the border position BP1; however, the border position BP1 will not be displayed on the ultrasonic image EG. The surface of the body of the target object is not included in the enlarged view of the specific area 52, and therefore the border position BP1 cannot be displayed.

The position output unit 33 calculates the coordinates of the display index PP1 based on the magnification percentage of the specific area 52 and the coordinate position of the specific index MK1. In probe display unit 13*a*, the display index PP1 is indicated with "□" mark, a mark with a same shape as the specific index MK1, on a position corresponding to the border position BP1. In the enlarged ultrasonic image EG, the specific index MK1 is positioned close to the center of the ultrasonic image EG; the display index PP1 is displayed on the left side of the probe display unit 13*a*.

FIG. 5(*b*) is an example of displaying the ultrasonic image EG at the same magnification, after setting the specific index MK1 on the enlarged ultrasonic image EG, as shown in FIG. 5(*a*). When the positions of the probe display unit 13*a* and the ultrasonic image EG are displayed at the same magnification, the positions to X-axis direction of the specific index MK1 and the display index PP1 correspond. In FIG. 5(*b*), another tumor TM is displayed in the specific region 54. The operator can indicate the center of the tumor TM by enlarging the specific region 54, as shown in FIG. 5(*b*), or indicate the center of the tumor TM in the specific region 54, at the same magnification, as shown in FIG. 5(*b*).

The display unit 50 is able to display the ultrasonic image EG with enlargement or reduction at arbitrary magnification. The border position BP1 and the display index PP1 are displayed in different positions, except when displaying the ultrasonic image EG at the same magnification. When the operator displays the ultrasonic image EG in an enlarged image, it is difficult to determine the position of the tumor displayed in the probe display unit 13*a*. However, in this embodiment, even when indicating the tumor TM by looking the enlarged ultrasonic image EG, it is able to determine the position on the surface of the body of the target object for puncturing a needle accurately.

Example of Displaying the Region (Range) Using an Index

In some cases, when exenterating tumors TM or foreign materials, it may be preferred to indicate the region (range) in the probe display unit 13*a*, instead of coordinates (points). The operator is able to plan the incision site, by marking the size and the position of the tumor TM on the surface of the body of the target object.

When setting range on the ultrasonic image EG, a method of setting two specific indices on the ultrasonic image EG, to indicate two display indices on the probe display unit 13*a*, is used. Also, a method of setting two specific indices on the ultrasonic image EG, to set one display region, is also used.

FIGS. 6(*a*) and 6(*b*) are schematic views illustrating the ultrasonic image EG, indicating the target tumor TM to be exenterated. FIG. 6(*a*) is a drawing indicating four displayed indices PP1-PP4, and FIG. 6(*b*) is a drawing indicating two displayed regions PA1-PA2 in the probe display unit 13*a*. In FIG. 6(*a*) and FIG. 6(*b*), the coordinates of the probe display unit 13*a* in the X-axis direction and the ultrasonic image EG in the X-axis direction are displayed at the same magnification.

For example, as indicated in FIG. 6(*a*), when the operator operates the linear ultrasonic probe 11*a* and displays the ultrasonic image EG of the tumor TM to be exenterated on the display unit 50, two parts of the tumor TM (TM1 and TM2) have bulged. The operator indicates four end points of the tumor TM that are parallel to X-axis of the surface of the body, using the input unit 40. The operator indicates two end points of the tumor TM1 on both ends and two end points of the tumor TM2 on both ends. Index input unit 32 sets the specific indices MK1-MK4, and indicates indices MK1 and MK2, indices with same height in the Z-axis direction, with "▼" mark, and indices MK3 and MK4, indices with same height in the Z-axis direction, with "□" mark. Index input unit 32 calculates four routes GL1-GL4, vertically connecting the specific indices MK1-MK4 and the surface of the body, and displays routes GL1-GL4 on the ultrasonic image EG. Also, intersections of each four routes GL1-GL4 and the surface of the body are calculated as four border positions BP1-BP4.

The position output unit 33 decodes the coordinates of the specific indices MK1-MK4, and converts to coordinates with diminishing scale for display on the probe display unit 13*a*. Also, because the probe display unit 13*a* of FIG. 6 has width in the Z-axis direction and can be displayed in two-dimension, the specific indices MK1-MK4 decodes the position of not only X-axis direction but also Z-axis direction.

The display indices PP1 and PP2 are set with the same "▼" mark, and the display indices PP3 and PP4 are set with same "□" mark on the lower side to Z-axis direction, so that the calculated coordinates correspond to the specific indices MK1-MK4. Thereby the size of the tumor TM with two bulges individually expanding to Z-axis direction can be displayed. The operator is able to mark four display indices PP1-PP4 on the surface of the body within the range of the tumor TM. The operator can easily distinguish the region of the tumor TM, if corresponding indices have same shape, to indicate the region (range).

As displayed in FIG. 6(*b*), two displayed regions PA1 and PA2 can be displayed, instead of displaying four specific indices MK1-MK4. The operator indicates one end to the other end of the tumor TM1 and indicates one end to the other end of the tumor TM2, both parallel to X-axis direction of the surface of the body. The index input unit 32 sets the specific region MA1 of one end to the other end of the tumor TM1, and sets the specific region MA2 of one end to the other end of the tumor TM2. Also, the index input unit 32 sets a color or a pattern on the specific region MA1 and specific region MA2, for differentiating thereof.

Also, because the probe display unit 13a of FIG. 6(b_has width in the Z-axis direction and can be displayed in two-dimension, the position output unit 33 decodes the coordinates of specific regions MA1 and MA2, and converts to the coordinates corresponding to the probe display unit 13a. In the probe display unit 13a, the display region PA1 and PA2 are displayed, for indicating the size of tumors TM1 and TM2, on different height to Z-axis direction. Also, the probe display unit 13a acquires the color or the pattern information of the specific region MA1 and MA2, displayed in the ultrasonic image EG. Thus, in the probe display unit 13a, the display regions PA1 and PA2 are displayed with same color or pattern of the corresponding specific region MA1 and MA2.

The operator is able to confirm the actual size of the specific regions MA1 and MA2, and mark the incision site on the surface of the body of the target object using the medical pen.

A detailed example of setting a plurality of specific regions MA, for avoiding the region above the tumor TM, is explained hereafter. When marking the shape and the range of the tumor TM on the surface of the body of the target object using the medical marker, the marking will be drawn on the surface of the body in two-dimension.

Figure 7A:
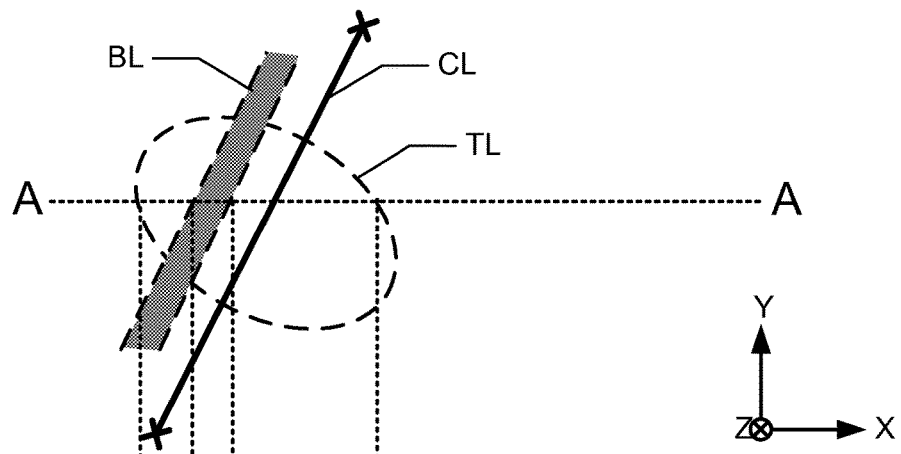
FIG. 7(a) is a diagram indicating an example of marking on the surface of a target object.

FIG. 7(a) is a detailed example of marking on the surface of the body using the probe display unit 13a. The operator can draw the tumor line TL as the contour of the tumor TM on the surface of the body, by altering the angle of the ultrasonic image EG of the tumor TM. At the same time, the operator can draw the blood vessel line BL, for the purpose of avoiding the blood vessel BV.

Figure 7B:
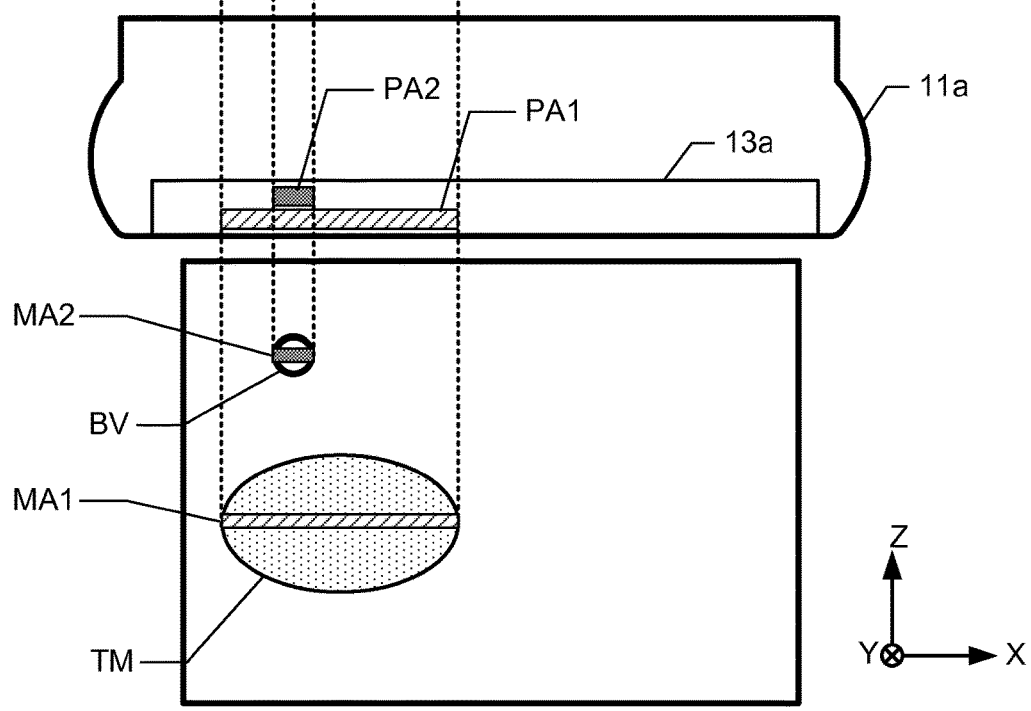
FIG. 7(b) is a schematic view of the ultrasonic image EG at line A-A shown in FIG. 7(a).

FIG. 7(b) is a schematic view of the ultrasonic image EG at line A-A shown in FIG. 7(a). The cross-section of the ultrasonic image EG at line A-A can be acquired by placing the linear ultrasonic probe 11a on the A-A line, shown in FIG. 7(a). As shown in FIG. 7(b), the tumor TM and blood vessel BV appears on the ultrasonic image EG. The operator indicates the specific region MA1 on the tumor TM, and indicates the specific region MA2 on blood vessel. The specific region MA1 and the specific region MA2 are displayed as the display region PA1 and the display region PA2 on the probe display unit 13a, respectively. The operator marks the display region PA1 and display region PA2 on the surface of the body. In FIG. 7(b), different colors between the specific region MA and the display region PA are indicated by different patterns.

The operator marks the display region PA1 and display region PA2 on the surface of the body, using either the ultrasonic image EG obtained by moving the A-A line, which also is a position of the linear ultrasonic probe 11a, in a parallel direction to the Y-axis direction, or the ultrasonic image EG obtained by rotating the A-A line at 180-degrees angle to the rotational direction. Thus, the operator can draw the tumor line TL and the blood vessel line BL in two-dimension on the surface of the body, as indicated in FIG. 7(a). Therefore, the operator is able to draw the incision line CL to identify the incising direction for performing a safe operation.

In FIGS. 6(a), 6(b), 7(a), and 7(b), the positions of the probe display unit 13a and the ultrasonic image EG are displayed at the same magnification. When the ultrasonic image EG is enlarged or reduced, the position output unit 33 converts coordinates of border positions into coordinates of the probe display unit 13a, in accordance to the magnification.

Figure 6A:
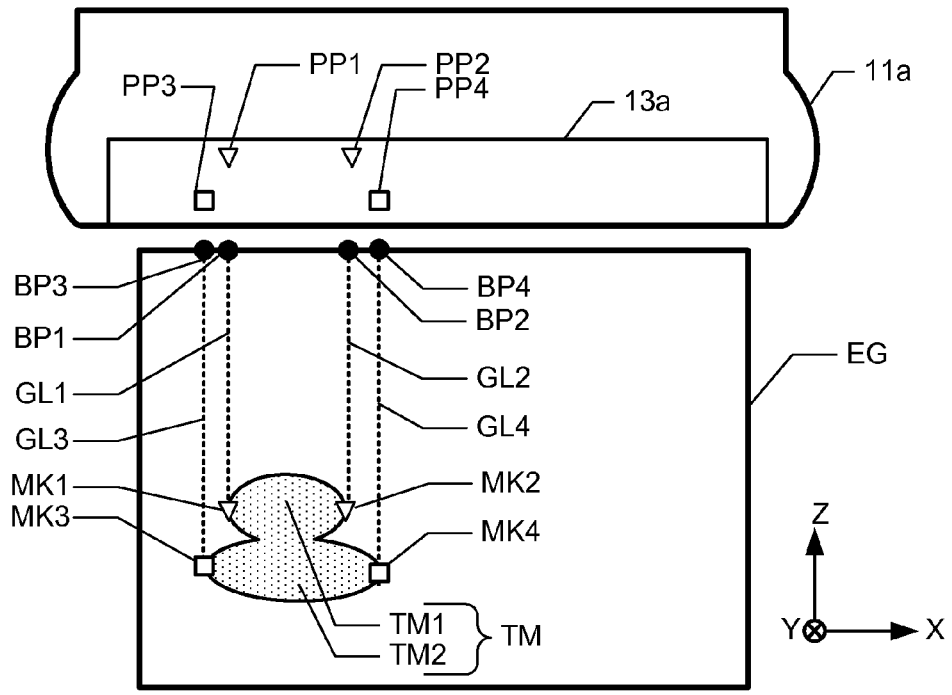
FIG. 6(a) is a diagram indicating two displayed indices PP1 and PP2.
Figure 6B:
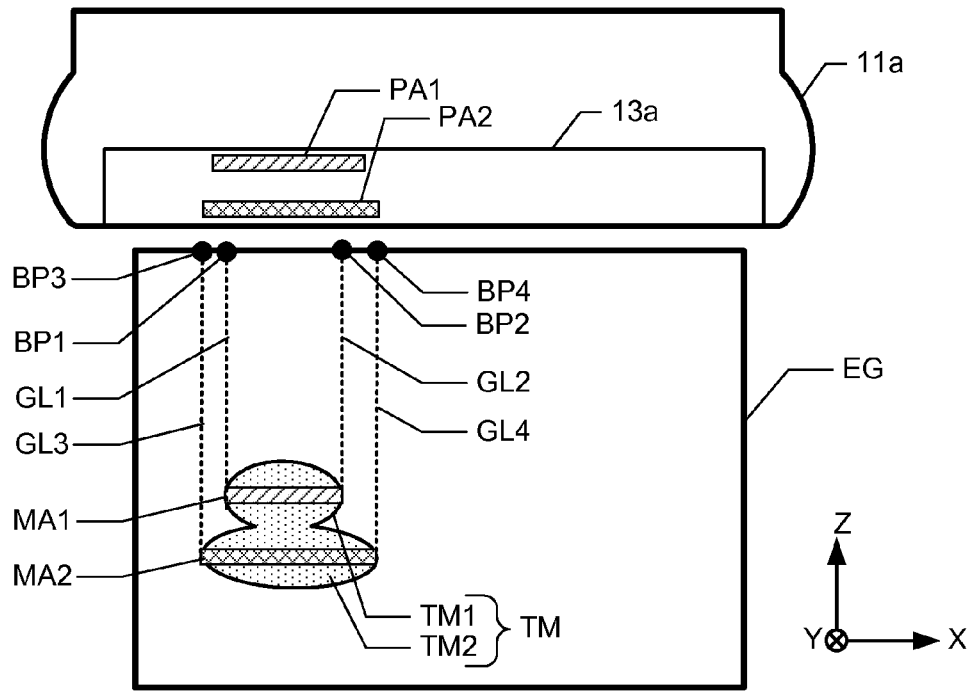
FIG. 6(b) is a diagram indicating one displayed region PA.

In FIG. 6(a), two routes GL1 and GL2, a route which two specific indices MK1 and MK2 and the surface of the body intersects vertically, and two border positions BP1 and BP2 are calculated, and displayed on the ultrasonic image EG. However, in case of marking range of the tumor TM on the surface of the body, two routes GL1 and GL2 and two border positions BP1 and BP2 can be eliminated from the display unit 50, since it is not necessary to tilt the route GL.

Second Embodiment

In the ultrasonic diagnostic apparatus of the second embodiment, the probe display unit 13a, explained in the first embodiment, is configured as a position display apparatus and as a removable form.

A benefit of changing the probe display unit 13a and the position display processing unit 34 into removable form is the increase in types of removable ultrasonic probe.

The configuration of the ultrasonic diagnostic apparatus 120 is similar to the configuration previously explained in the first configuration; therefore, same numberings are used for the same configurations and explanation of the same configuration previously explained is omitted.

The ultrasonic probe having a removable position display unit can be used, not only with the linear ultrasonic probe 11a described in the first embodiment, but also with a convex ultrasonic probe 11b or a sector ultrasonic probe 11c. An example of fixing the probe display unit 13a to the convex ultrasonic probe 11b and the sector ultrasonic probe 11c is explained hereafter. Although it is not described in the figure, the position display apparatus has a fixing apparatus, such as clip, on the probe display unit 13a.

Figure 8A:
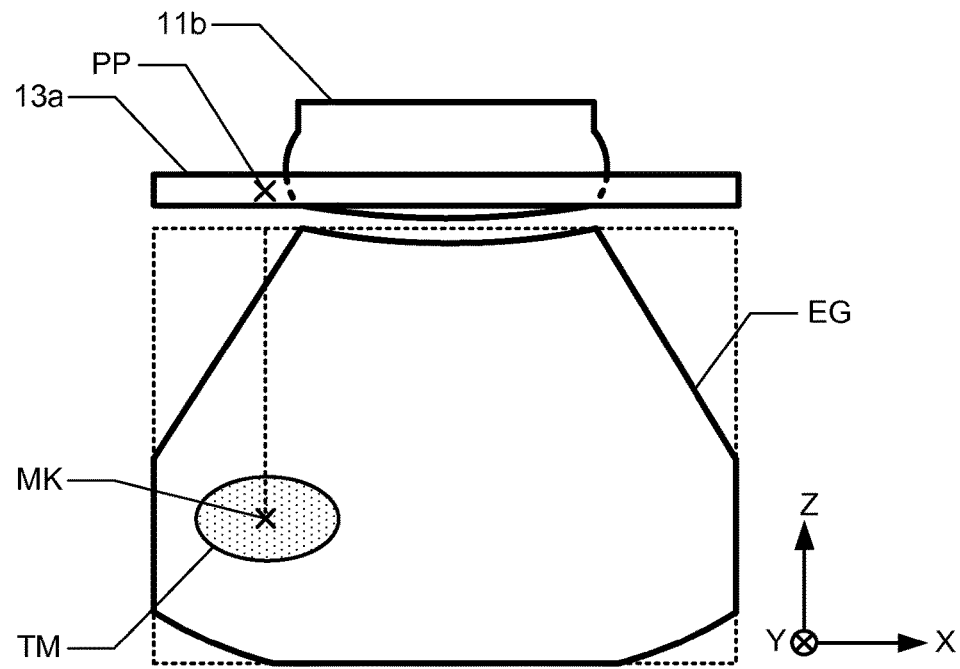
FIG. 8(a) is a schematic view of fixing a probe display unit onto a convex ultrasonic probe.

When the ultrasonic diagnostic apparatus 120 wants to mark an index on surface of the body, the probe display unit 13a is fixed to predetermined ultrasonic probe. FIG. 8(a) is a schematic view of fixing the probe display unit 13a onto the convex ultrasonic probe 11b.

Because the ultrasonic transducer (not described on figure) of the convex ultrasonic probe 11b is formed in a fan-shape, the ultrasonic image EG is displayed in a fan-shape. As shown in FIG. 8(a), the ultrasonic image EG is a cross-sectional image spreading from the contact point of the convex ultrasonic probe 11b and the surface of the body. Also, the probe display unit 13a is formed in range that can be acquired by the convex ultrasonic probe 11b in the X-axis direction.

The position output unit 33 (refer to FIG. 1) of the ultrasonic diagnostic apparatus corrects the coordinates of the specific indices MK of the ultrasonic image EG spreading to fanwise direction in accordance to the information acquired from the convex ultrasonic probe 11b, converts to the coordinates of the probe display unit 13a and displays in actual dimension. Also, the ultrasonic diagnostic apparatus 120 stores the corrected value of the coordinates of ultrasonic image EG acquired by convex ultrasonic probe 11b, in the memory 20.

The probe display unit 13a displays the position information of acquired specific index MK as the display index PP, based on the shape of the index or additional information such as color.

Figure 8B:
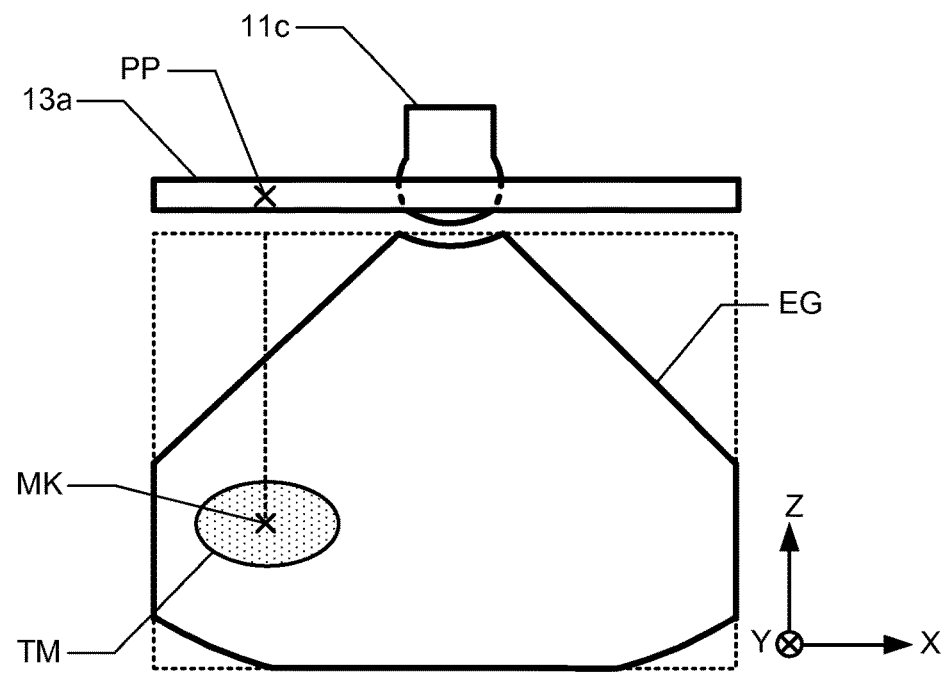
FIG. 8(b) is a schematic view of fixing the probe display unit 13a onto the sector ultrasonic probe 11c.

FIG. 8(b) is a schematic view of fixing the probe display unit 13a onto the sector ultrasonic probe 11c. The sector ultrasonic probe 11c is configured with narrower ultrasonic transducer (not shown), in comparison to the convex ultrasonic probe 11b, and its ultrasonic image EG is displayed in fan shape.

As shown in FIG. 8(b), the sector ultrasonic probe 11c is configured in a way that it has smaller contact point than the convex ultrasonic probe 11b, shown in FIG. 8(a). Also, the ultrasonic image spreads to fanwise direction, in comparison to the ultrasonic probe 11b.

Similarly, the position output unit 33 of the ultrasonic diagnostic apparatus 120 corrects the coordinates of the specific index MK of the ultrasonic image EG spreading to fanwise direction in accordance to the information acquired from the sector ultrasonic probe 11c, converts to the coordinates of the probe display unit 13a and displays in actual dimension. Also, the ultrasonic diagnostic apparatus 120 stores the corrected value of the coordinates of ultrasonic image EG acquired by convex ultrasonic probe 11c, in the memory 20.

In this embodiment, the specific index MK was used for explanation; similar to the first embodiment, the specific region MA can be displayed in the probe display unit 13a.

Third Embodiment

The probe display unit 13a in the first embodiment and the second embodiment indicated the position of the ultrasonic probe in a long axis direction (X-axis direction). On the two-dimensional ultrasonic probe 11d in the third embodiment, a probe display unit 13b is fixed to the two-dimensional ultrasonic probe 11d in a short-axis direction (Y-axis direction). Two-dimensional ultrasonic probe 11d is used in the ultrasonic diagnostic apparatus indicated in the first embodiment and the second embodiment. An example of fixing the two-dimensional ultrasonic probe 11d to the ultrasonic diagnostic apparatus of the first embodiment is explained below. Same numberings are used for the same configurations and explanation of the same configuration previously explained is omitted.

Figure 9:
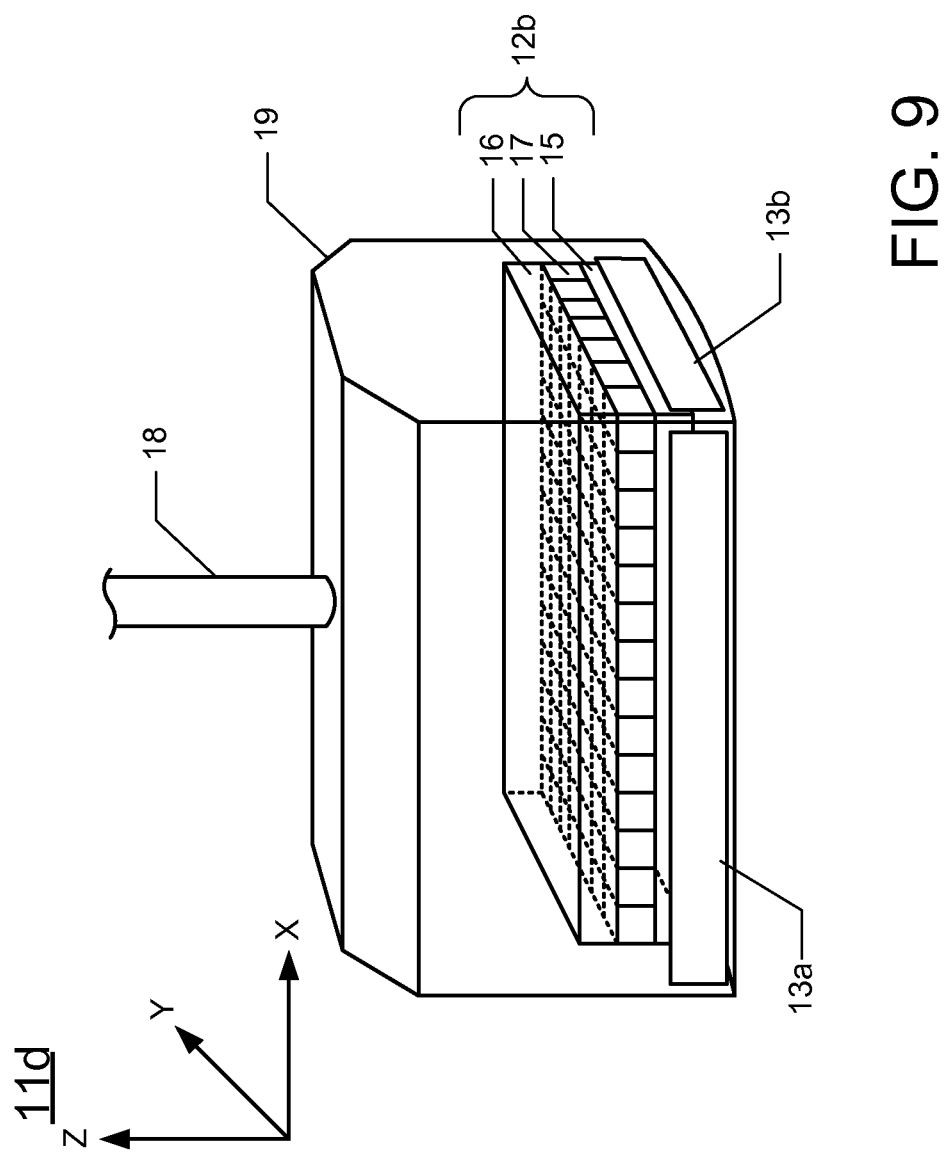
FIG. 9 is a perspective view of a configuration of a two-dimensional ultrasonic probe.

The two-dimensional ultrasonic probe 11d in this embodiment includes matrix array transducer 17, placed in two-dimensional form. FIG. 9 is a perspective view of the configuration of two-dimensional ultrasonic probe 11d.

As shown in FIG. 9, two-dimensional ultrasonic probe 11d includes a case 19, a transducer unit 12b, a probe display unit 13a, 13b and a cable 18. FIG. 2 describes the inner configuration of the two-dimensional ultrasonic probe 11b to provide a better understanding.

In the two-dimensional ultrasonic probe 11d, embedded transducer unit 12b and the probe display unit 13a and 13b communicate with the transmitting/receiving unit 10 and CPU 30 (refer to FIG. 1) through the parallel bus PB. As indicated in FIG. 9, the transducer unit 12b includes a matrix array transducer 17, a matching layer 15 and a backing material 16.

The matrix array transducer 17 is configured with a plurality of ultrasonic transducers placed in two-dimension in the X-axis direction and Y-axis direction. The transmitting/receiving unit 10 drives the matrix array transducer 17, to form ultrasonic beam scanning the preset three-dimensional region of interest. Transmitted ultrasonic beam reflects inside the target object, and the reflected wave is received by the matrix array transducer 17. Transmitting/receiving unit 10 amplifies and delays signals received in the matrix array transducer 17, and generates a plurality of beamforming signal corresponding to the region of interest. Image processing unit 31 generates the rendering image of the region of interest based on preset perspective, by processing the beamforming signal, generated in the matrix array transducer 17. The display unit 50 displays the rendering image generated by the image processing unit 31.

Therefore, the matrix array transducer 17 can acquire a volume rendering image on a plurality of three-dimensional regions, by performing a scan using the ultrasonic on a plurality of three-dimensional regions, setting perspective points independently on each scan region, and displaying a plurality of images in a parallel manner. Thereby the matrix array transducer 17 can scan a plurality of three-dimensional region of interest in high speed.

Probe display unit 13a and the probe display unit 13b are configured with a liquid crystal panel. The probe display unit 13a is positioned in the two-dimensional ultrasonic probe 11d in the long axis (X-axis) direction and the probe display unit 13b is positioned in the two-dimensional ultrasonic probe 11d in the short axis (Y-axis) direction.

The index input unit 32 sets the specific region MK from the rendering image, the position output unit converts the specific index MK into the real-size coordinates, and divides into the position in the X-axis and Y-axis directions for outputting.

The probe display unit 13a displays the position of the specific index MK in the X-axis direction with the index. The probe display unit 13b displays the position of the specific index MK in the Y-axis direction with the index. Also, the probe display unit 13a and the probe display unit 13b can display not only the specific index MK but also the specific region MA.

In the third embodiment, the probe display unit 13a and the probe display unit 13b are fixed to the two-dimensional ultrasonic probe 11d; however, as indicted in the second embodiment, removable probe display unit 13a and probe display unit 13b can be used.

Fourth Embodiment

In the ultrasonic diagnostic apparatus 100 in the fourth embodiment, the range of the blood vessel can be detected to display on the ultrasonic probe 11. The blood flowing detecting unit 39, a part which detects the blood flowing region, is explained below.

In the first embodiment, puncturing a needle to the tumor using the ultrasonic diagnostic apparatus 100 was explained; the same method can be applied for puncturing a needle to the blood vessel BV. In the fourth embodiment, a case of an operator selecting the blood vessel puncturing mode in the ultrasonic diagnostic apparatus 100, is explained.

In the input unit 40, the blood vessel puncturing mode is selected, and the blood flowing region detecting unit 39 of CPU 30 starts the operation (refer to FIG. 1). Blood flowing region detecting unit 39 is processed in background, and the operator is able to confirm the processing result of the blood flowing region detecting unit 39 through the probe display unit 13a of the ultrasonic probe 11. The blood flowing region detecting unit 39 obtains Doppler information calculated by the image processing unit 31, and detects the blood vessel BV. Also, the blood flowing region detecting unit 39 can automatically transmit the coordinate signal to the position output unit 33.

Figure 10:
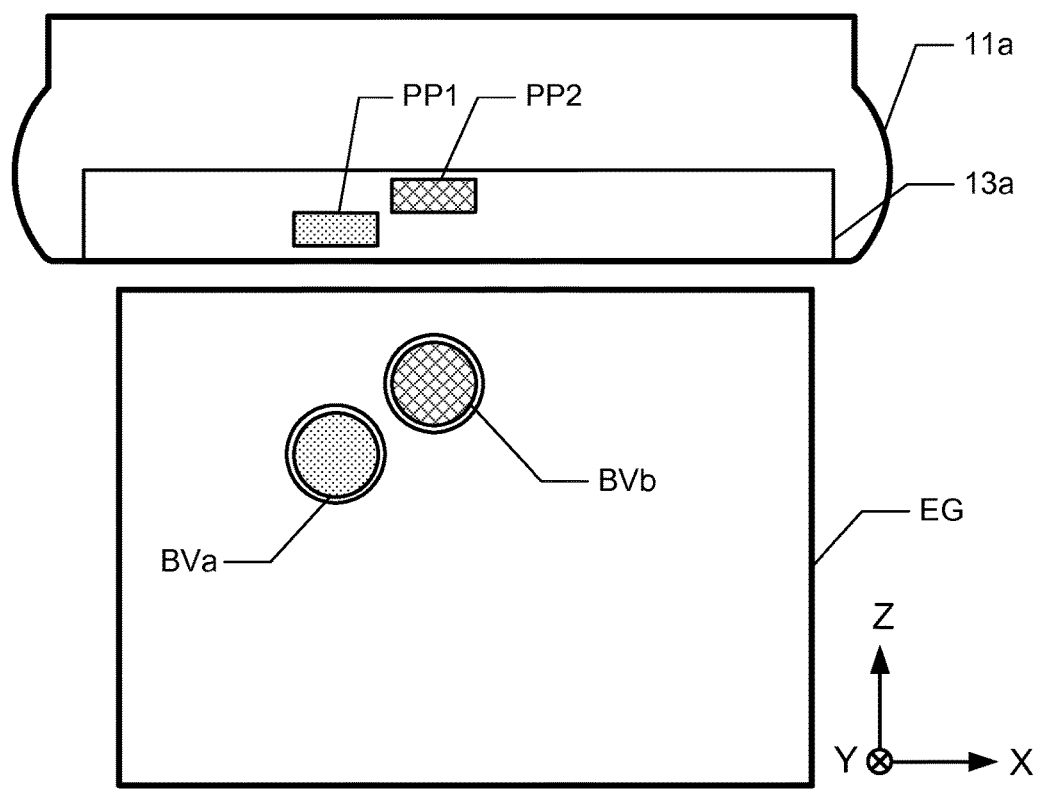
FIG. 10 is a diagram illustrating the detection of artery BVa and vein BVb on the ultrasonic image EG.

FIG. 10 is a diagram illustrating the detection of artery BVa and vein BVb on the ultrasonic image EG. As shown in FIG. 10, the short axis images of the blood vessel BV of artery BVa and vein BVb are displayed. The blood flowing region detecting unit 39 recognizes the blood vessel BV from the Doppler information, and once the blood vessel BV is identified as either artery BVa or vein BVb, the ultrasonic image EG displays its region on top of the ultrasonic image EG as color information. For example, artery BVa can be displayed in red color, and vein BVb can be displayed in blue color.

The blood flowing region detecting unit 39 acquires the range of artery BVa and vein BVb in the X-axis direction, the position of Y-axis and the color information, and transmits to the position output unit 33. The position output unit 33 converts to the position and the width of the short axis image (diameter of blood vessel) in actual size, and transmits to the probe display unit 13a. The probe display unit 13a can display the position of the artery BVa and vein BVb as the display region PA1 and the display region PA2, respectively.

The ultrasonic diagnostic apparatus 100 can always display the detected blood vessel BV on the probe display unit 13a while operating the blood flowing region detecting unit 39; therefore, when the operator changes the displaying angle of the blood vessel BV from the short axis direction to the long axis direction, the operator can confirm whether the desired blood vessel BV is artery BVa or vein BVb. For example, when the ultrasonic probe 11 is positioned on top of the artery BVa, the color of the probe display unit 13a turns red.

Also, in case of the ultrasonic probe 11d consisting of the matrix array transducer 17 as indicated in the fourth embodiment, even if the image of the blood vessel to the long axis direction is captured, the position of the blood vessel BV thereof can be displayed on the probe display unit 13b.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An ultrasonic diagnostic apparatus comprising:
   a display unit configured to display a two-dimensional ultrasonic image;
   a central processing unit connected to the display unit;
   an ultrasonic probe connected to the central processing unit, wherein the ultrasonic probe includes a probe display unit fixed to the ultrasonic probe and;
   a display control unit implemented using the central processing unit, wherein the display control unit is configured to display, based on specific information that indicates at least one of a pair of specific points and a specific line in the two-dimensional ultrasonic image displayed on the display unit, at least one of a pair of points and a line corresponding to the at least one of the pair of specific points and the specific line on the probe display unit of the ultrasonic probe;
   an index input unit implemented using the central processing unit, wherein the index input unit is configured to calculate routes from one of i) the pair of specific points to a surface of a target object in the two-dimensional image in the two-dimensional ultrasonic image and ii) a first end and a second end of the specific line to the surface of the target object in the two-dimensional ultrasonic image, wherein the index input unit is configured to determine intersection points of the routes and the surface of the target object in the two-dimensional ultrasonic image;
   a position output unit implemented using the central processing unit, wherein the position output unit is configured to convert the intersection points to coordinates corresponding to the probe display unit; and
   wherein the display control unit is further configured to display the intersection points at respective positions corresponding to the coordinates on the probe display unit.

2. The ultrasonic probe of claim 1, wherein the specific information is both end parts of a site of the target object in the predetermined direction, and said display control unit is configured to separate both end parts to display two points on said probe display unit.

3. The ultrasonic probe of claim 1, wherein the specific information is a width of a site of the target object in a predetermined direction, and wherein the display control unit is configured to display a region of the width on said probe display unit.

4. The ultrasonic diagnostic apparatus of claim 1, wherein the specific information indicates a first specific point or line and a second specific point or line, that is different from the first specific point or line, on the two-dimensional ultrasonic image, and wherein said display control unit is configured to display the first specific point or line and the second specific point or line on the probe display unit in an identifiable manner along a predetermined direction.

5. The ultrasonic diagnostic apparatus of claim 1, wherein the probe display unit is oriented in a predetermined direction.

6. The ultrasonic diagnostic apparatus of claim 1, wherein the specific information indicates a first specific point or line and second specific point or line that is different from the first specific point or line, and wherein the display control unit is configured to display the first specific point or line and the second specific point or line in an identifiable manner along a direction orthogonal to a predetermined direction.

7. The ultrasonic diagnostic apparatus of claim 1, wherein the ultrasonic probe comprises a transducer array aligned in a predetermined direction and configured to transmit an ultrasonic beam to the target object and receive a reflected ultrasonic beam from the target object.

8. The ultrasonic diagnostic apparatus of claim 7, wherein the probe display unit has a length at least as long as a length of the transducer array.

9. An ultrasonic diagnostic method performed by an ultrasonic diagnostic apparatus, the method comprising:
   displaying a two-dimensional ultrasonic image on an image display unit;
   based on specific information that indicates at least one of a pair of specific points and a specific line in the two-dimensional ultrasonic image displayed on the image display unit, displaying, by a display control unit implemented using a central processing unit (CPU), at least one of a point and a line corresponding to the at least one of the pair of specific points and the specific line on a probe display unit of an ultrasonic probe connected to the CPU, wherein the probe display unit is fixed to the ultrasonic probe and is configured to display at least the pair of specific points and the specific line;
   calculating, by an index input unit implemented using the CPU, routes from one of i) the pair of specific points to a surface of a target object in the two-dimensional ultrasonic image and ii) a first end and a second end of the specific line to the surface of the target object in the two-dimensional ultrasonic image;
   determining, by the index input unit, intersection points of the routes and the surface of the target object in the two-dimensional ultrasound image;

converting the intersection points to coordinates corresponding to the probe display unit; and
displaying the intersection points at respective positions corresponding to the coordinates on the probe display unit after said converting.

10. The method of claim 9, wherein the specific information indicates on the two-dimensional ultrasonic image a first specific point or line and a second specific point or line that is different from the first specific point or line, and wherein said display control unit is configured to display the first specific point or line and the second specific point or line on the probe display unit in an identifiable manner along a predetermined direction.

11. The method of claim 9, wherein the specific information indicates a first specific point or line and second specific point or line that is different from the first specific point or line, and wherein said display control unit is configured to display the first specific point or line and the second specific point or line in an identifiable manner along a direction orthogonal to a predetermined direction.

12. The method of claim 9, wherein the specific information comprises a blood flowing region detected by a blood flowing region detecting unit.

13. The method of claim 9, wherein the probe display unit has a length at least as long as a length of a transducer array in the ultrasonic probe.

14. The method of claim 13, wherein the probe display unit is oriented in a predetermined direction that the transducer array is oriented in.

15. An ultrasonic diagnostic system comprising:
an ultrasonic diagnostic apparatus comprising:
an image display unit configured to display a two-dimensional ultrasonic image;
an index input unit configured to input specific information, wherein the specific information indicates at least one of a pair of specific points and a specific line on the two-dimensional ultrasonic image displayed on said image display unit, wherein said index input unit is configured to calculate routes from one of i) the pair of specific points to a surface of a target object in the two-dimensional ultrasonic image and ii) a first end and a second end of the specific line to the surface of the target object in the two-dimensional ultrasonic image, wherein said index input unit is configured to determine intersection points of the routes and the surface of the target object in the two-dimensional ultrasonic image;
a display control unit configured to display at least one of a pair of points and a line corresponding to the at least one of the pair of specific points and the specific line on a probe display unit;
a position output unit configured to convert the intersection points to coordinates corresponding to the probe display unit;
wherein said index input unit, display control unit and said position output unit are implemented using a central processing unit; and
an ultrasonic probe comprising;
a transducer array oriented in a predetermined direction and configured to transmit an ultrasound beam to the target object and receive a reflected ultrasound beam from the target object;
the probe display unit coupled to said ultrasonic probe and wherein the probe display unit has a length at least as long as a length of the transducer array; and
a cable extending from said ultrasonic probe to said ultrasonic diagnostic apparatus, said cable configured to couple said ultrasonic probe to said ultrasonic diagnostic apparatus,
wherein the display control unit is further configured to display the intersection points at respective positions corresponding to the coordinates on the probe display unit.

16. The ultrasonic diagnostic system of claim 15, wherein the specific information indicates a first specific point or line and a second specific point or line, that is different from the first specific point or line, on the two-dimensional ultrasonic image, and wherein said display control unit is configured to display the first specific point or line and the second specific point or line on the probe display unit in an identifiable manner along the predetermined direction.

17. The ultrasonic diagnostic system of claim 15, wherein the specific information indicates a first specific point or line and second specific point or line that is different from the first specific point or line, and wherein said display control unit is configured to display the first specific point or line and the second specific point or line in an identifiable manner along a direction orthogonal to the predetermined direction.

18. The ultrasonic diagnostic system of claim 15, wherein the ultrasonic diagnostic apparatus further comprises a blood flowing region detecting unit configured to detect a blood flowing region of the target object, wherein said index input unit is configured to input the blood flowing region detected by said blood flowing region detecting unit as the specific information.

19. The ultrasonic diagnostic system of claim 15, wherein said index input unit includes a touch panel coupled to a surface of said image display unit.

20. The ultrasonic diagnostic system of claim 15, wherein the specific information indicates both end parts of a site of the target object in the predetermined direction, and wherein said display control unit is configured to separate both end parts to display the pair of points on the probe display unit.

21. The ultrasonic diagnostic system of claim 15, wherein the specific information indicates a width of a site of the target object in the predetermined direction, and wherein said display control unit is configured to display the region of the width in said probe display unit.

22. The ultrasonic diagnostic system of claim 15, wherein the probe display unit is oriented in the predetermined direction.

* * * * *